United States Patent [19]
Lally et al.

[11] Patent Number: 6,090,278
[45] Date of Patent: *Jul. 18, 2000

[54] APPARATUS AND METHOD FOR SEALING A PLURALITY OF CHROMATOGRAPHY COLUMNS

[75] Inventors: Michael T. Lally; Peter J. Leavesley, both of Charlottesville; Robert D. Lockman, Waynesboro; Peter C. Van Davelaar, Maidens, all of Va.

[73] Assignee: Dyax Corporation, Cambridge, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 09/137,264

[22] Filed: Aug. 20, 1998

[51] Int. Cl.$^7$ .................................................. B01D 15/08
[52] U.S. Cl. ........................ 210/198.2; 210/656; 96/101; 96/106
[58] Field of Search .................................... 210/635, 656, 210/659, 198.2, 232, 238, 282; 96/101, 106

[56] References Cited

U.S. PATENT DOCUMENTS

| | | | |
|---|---|---|---|
| 3,483,986 | 12/1969 | Wright | 210/198 |
| 3,682,315 | 8/1972 | Haller | 210/198 |
| 4,250,035 | 2/1981 | McDonald et al. | 210/198.2 |
| 4,597,866 | 7/1986 | Couillard | 210/198.2 |
| 4,604,198 | 8/1986 | Dailey | 210/198.2 |
| 4,636,315 | 1/1987 | Allen | 210/198.2 |
| 4,766,082 | 8/1988 | D'Autry | 210/198.2 |
| 4,994,180 | 2/1991 | Sims et al. | 210/198.2 |
| 5,107,908 | 4/1992 | Newhouse | 210/198.2 |
| 5,228,988 | 7/1993 | Sanford | 210/198.2 |
| 5,238,556 | 8/1993 | Shirkhan | 210/198.2 |
| 5,286,652 | 2/1994 | James | 210/198.2 |
| 5,340,474 | 8/1994 | Kauver | 210/198.2 |
| 5,395,521 | 3/1995 | Jagadeeswaran | 210/198.2 |
| 5,397,462 | 3/1995 | Higashijima | 210/136 |
| 5,443,734 | 8/1995 | Fetner | 210/198.2 |
| 5,496,473 | 3/1996 | Chow | 210/198.2 |
| 5,512,168 | 4/1996 | Fetner | 210/198.2 |
| 5,531,959 | 7/1996 | Johnson | 210/198.2 |
| 5,585,070 | 12/1996 | Lessard | 210/198.2 |
| 5,601,707 | 2/1997 | Clay | 210/198.2 |
| 5,601,708 | 2/1997 | Leavesley | 210/198.2 |
| 5,714,074 | 2/1998 | Karlsson | 210/198.2 |
| 5,772,875 | 6/1998 | Pettersson | 210/198.2 |
| 5,866,008 | 2/1999 | Shalon | 210/198.2 |
| 5,872,010 | 2/1999 | Karger | 210/198.2 |
| 5,893,971 | 4/1999 | Shalon | 210/198.2 |
| 5,919,361 | 7/1999 | Moran | 210/198.2 |
| 5,951,873 | 9/1999 | Shalon | 210/198.2 |

OTHER PUBLICATIONS

Biotage brochure, Parallex HPLC, "Parallel Purification for Combinatorial Chemistry" pp. 1–5 undated.

*Primary Examiner*—Ernest G. Therkorn
*Attorney, Agent, or Firm*—Fish & Richardson P.C.

[57] ABSTRACT

An apparatus and method for sealing a plurality of columns containing media for use in liquid chromatography. The invention involves two sealing assemblies, each having a plurality of sealing heads. The sealing heads are sized to receive ends of the columns and to seal the columns when the heads are compressed. Compressive force is exerted by or through springs to permit the sealing heads to adapt to the length of the media bed within each column. The apparatus may include a pressure containment vessel for subjecting the columns to radial compression.

37 Claims, 12 Drawing Sheets

APPARATUS AND METHOD FOR SEALING A PLURALITY OF CHROMATOGRAPHY COLUMNS

BACKGROUND OF THE INVENTION

The invention relates to sealing a plurality of columns for performing liquid chromatography analyses.

Liquid chromatography is a technique for separating the individual compounds that exist in a subject sample. In employing the technique, the subject sample is carried in a liquid, called a mobile phase. The mobile phase carrying the subject sample is caused to migrate through a media, called a stationary phase. Different compounds will have differing rates of migration through the media, which effects the separation of the components in the subject sample. Liquid chromatography is commonly performed with reusable or disposable columns, both of which are usually cylindrical, in which the media bed is bounded axially by porous plates, or by plates containing defined flowpaths, through which the mobile phase will flow. (See U.S. Pat. No. 5,601,708 to Leavesley, and U.S. Pat. No. 4,250,035 to McDonald et al.)

SUMMARY OF THE INVENTION

The invention in general relates to sealing flowpath connections for a plurality of chromatography columns. The apparatus involves an upper sealing assembly and a lower sealing assembly. The upper sealing assembly includes a plurality of upper sealing heads and the lower sealing assembly includes a plurality of lower sealing heads. Each sealing head defines a flowpath for the passage of liquids. Both the upper and the lower sealing heads are sized to receive the open ends of the chromatography columns. Each of the upper sealing heads is aligned with one of the lower sealing heads.

In operation, chromatography columns are fitted between one of the lower sealing heads and the corresponding upper sealing head. Compressive forces are applied to each corresponding pair of the upper and the lower sealing heads that retain a chromatography column. The compressive forces may be applied by pressing the sealing heads against media beds in the columns and thus causing the sealing heads to create seals with the chromatography columns. In order to remove or change any of the chromatography columns, the compressive forces are reduced so as to release the seals created between the sealing heads and the chromatography columns and to facilitate the separation of the columns from the upper and lower sealing assemblies. Any tubing connected to the sealing assemblies may remain in place when the sealing heads are removed from the columns.

In preferred embodiments, the apparatus also involves a pressure containment vessel that surrounds the chromatography columns. Radial compressive force on the chromatography columns may be increased by introducing a pressurized fluid into a radial compression inlet in the pressure containment vessel. In these embodiments, the upper sealing assembly also includes an upper plate through which the upper sealing heads are fitted. The lower sealing assembly also includes a lower plate through which the lower sealing heads are slidably fitted. The upper plate and the lower plate are sized to close the pressure containment vessel. Clamps are used to secure the upper plate to the pressure containment vessel. In some preferred embodiments, the upper sealing assembly may slide on rails into alignment with the lower sealing assembly. Guides are situated within the pressure containment vessel to locate the chromatography columns between opposing upper and lower sealing heads. Elastomeric elements are employed to create seals between the upper plate and the pressure containment vessel, between the lower plate and the pressure containment vessel, and between each sealing head and either the upper plate or the lower plate.

The compressive force required to seal the columns may be supplied by any desired mechanism that can supply a compressive force to the sealing heads. A mechanism with an hydraulic piston may be used to supply the compressive force. The piston may transmit compressive force through a pivot arm or other linkage. Preferably, a compressive force is supplied to the sealing heads through springs. The springs may be subjected to a preload force. Alternately, the springs may be disposed so as to supply the necessary compressive force themselves. In such an embodiment, the piston may be used to provide additional compressive force to the springs, in order to reduce the compression on the lower sealing heads, the media beds, and the upper sealing heads, so that the columns may be inserted into or removed from the apparatus.

Preferred embodiments employ sealing heads that can be inserted into columns with low insertion force; however, embodiments of the invention may employ any type of sealing head. For example, the columns may be sealed by forcing a one-piece sealing head with an elastomeric o-ring (connected radially or to an end of the sealing head) into the columns. Alternately, tapered sealing heads can be forced into a column without employing an o-ring to create a seal. Other types of sealing heads employ o-rings or knife edges (see U.S. Pat. No. 5,601,708 to Leavesley) oriented axially on a sealing head that creates seals with the edges of an open end of a column.

Embodiments of the invention may include one or more of the following advantages. The sealing assemblies can create secure seals in a plurality of chromatography columns simultaneously. Embodiments of the invention can limit the gap between the media bed and the sealing heads in a column that is positioned for chromatographic analysis. Seals can be created in a plurality of columns having media beds of differing lengths. Sealing heads may move independently of each other in order to create effective seals in a plurality of columns having media beds of differing lengths. Embodiments of the invention may be used with a variety of different types of sealing heads. A plurality of columns may be subjected to chromatography analyses at one time. Changing or replacing columns is simplified because all sealing heads can be removed by removing the upper sealing assembly and because all fluid connections may remain attached to the sealing heads in the sealing assemblies. Embodiments of the invention may be used with either disposable or reusable chromatography columns. Embodiments of the invention may be used with either flexible-walled or rigid-walled chromatography columns. A plurality of chromatography columns can be subjected to similar axial or radial compressive forces or to a combination of both axial and radial compressive forces. Axial and radial compressive forces applied to the chromatography columns compress the media beds, giving the media a more uniform consistency and making the columns more reliable for chromatographic analysis. The operation of closing and clamping the upper sealing assembly and the operation of sealing the columns are separated. The pressure containment vessel may be closed without having to apply enough force either to seal the chromatography columns or to provide axial or compressive forces to the media beds; thus, the design of the upper sealing assembly is simplified (as levers or linkages are not required to apply these forces) and the effort required by the operator is reduced and simplified, as well. Separate mechanisms may be employed to supply the forces needed to seal the chromatography columns and to supply radial compressive forces to the columns. Additional axial compressive force may be provided to the media bed beyond any force needed to seal the chromatography columns. In alternative embodiments, the force required to activate the sealing heads or to provide axial compression may be supplied by springs, as opposed to an hydraulic or similar mechanism, so that loss of force from the hydraulic or similar mechanism will not impair the seals between the sealing heads and the columns.

Additionally, using embodiments of the invention can simplify the performance of chromatography analyses with a large throughput volume of mobile phase and subject sample. For example, embodiments of the invention can be used to purify or analyze several different samples using one type of media in a chromatography column, or a single sample with several different types of media, each in a different column. Embodiments of the invention also facilitate the division of a large sample into smaller samples, in order to increase the amount of material that may be purified in a given time with a single type of chromatography media and solvent system.

Other features and advantages of the invention will be apparent from the following description of the preferred embodiments thereof and from the claims.

DESCRIPTION OF THE PREFERRED EMBODIMENTS

Figure 1A:
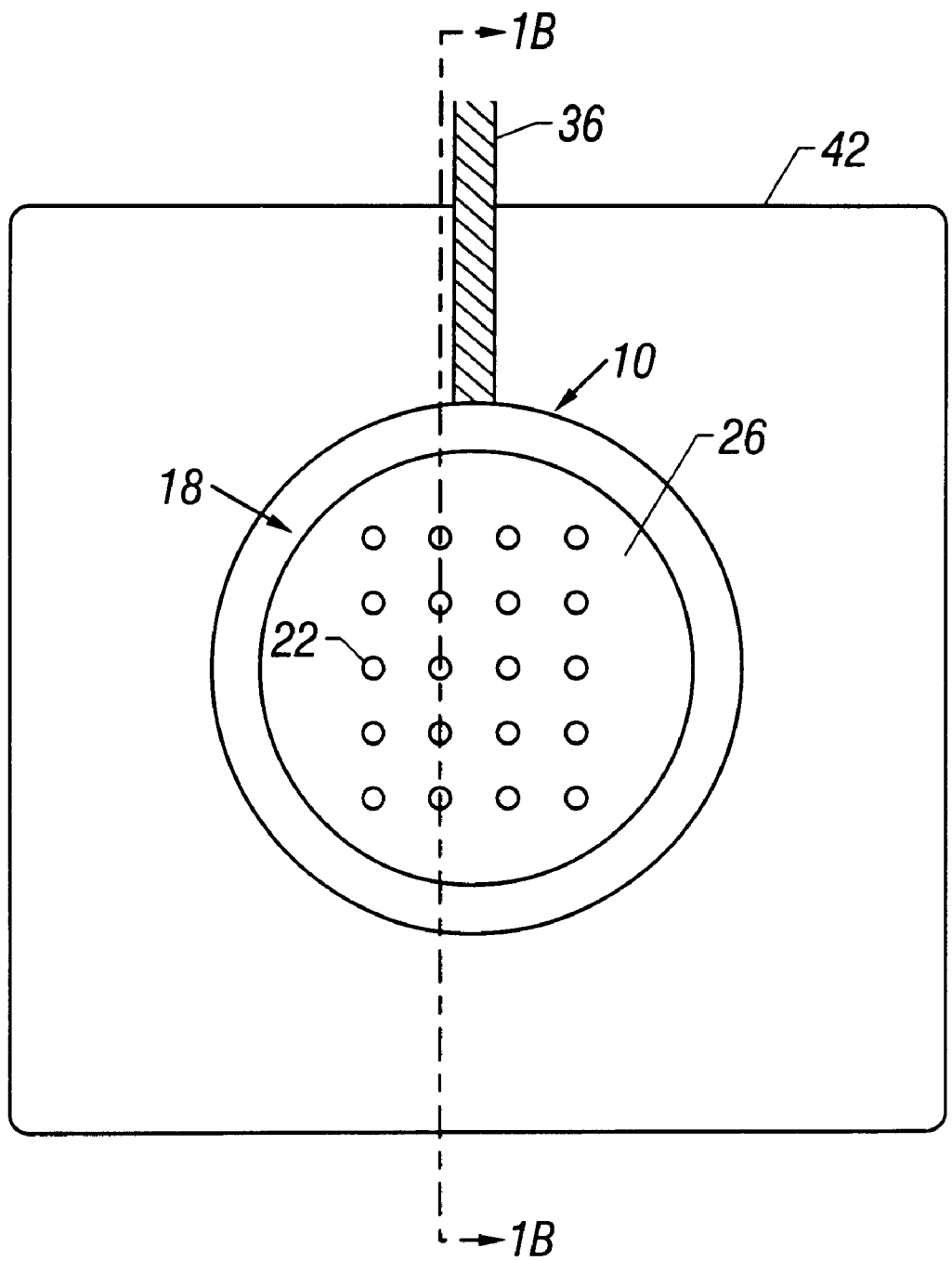
FIG. 1A is a diagrammatic plan view of an apparatus for sealing a plurality of chromatography columns according to the invention.
Figure 1B:
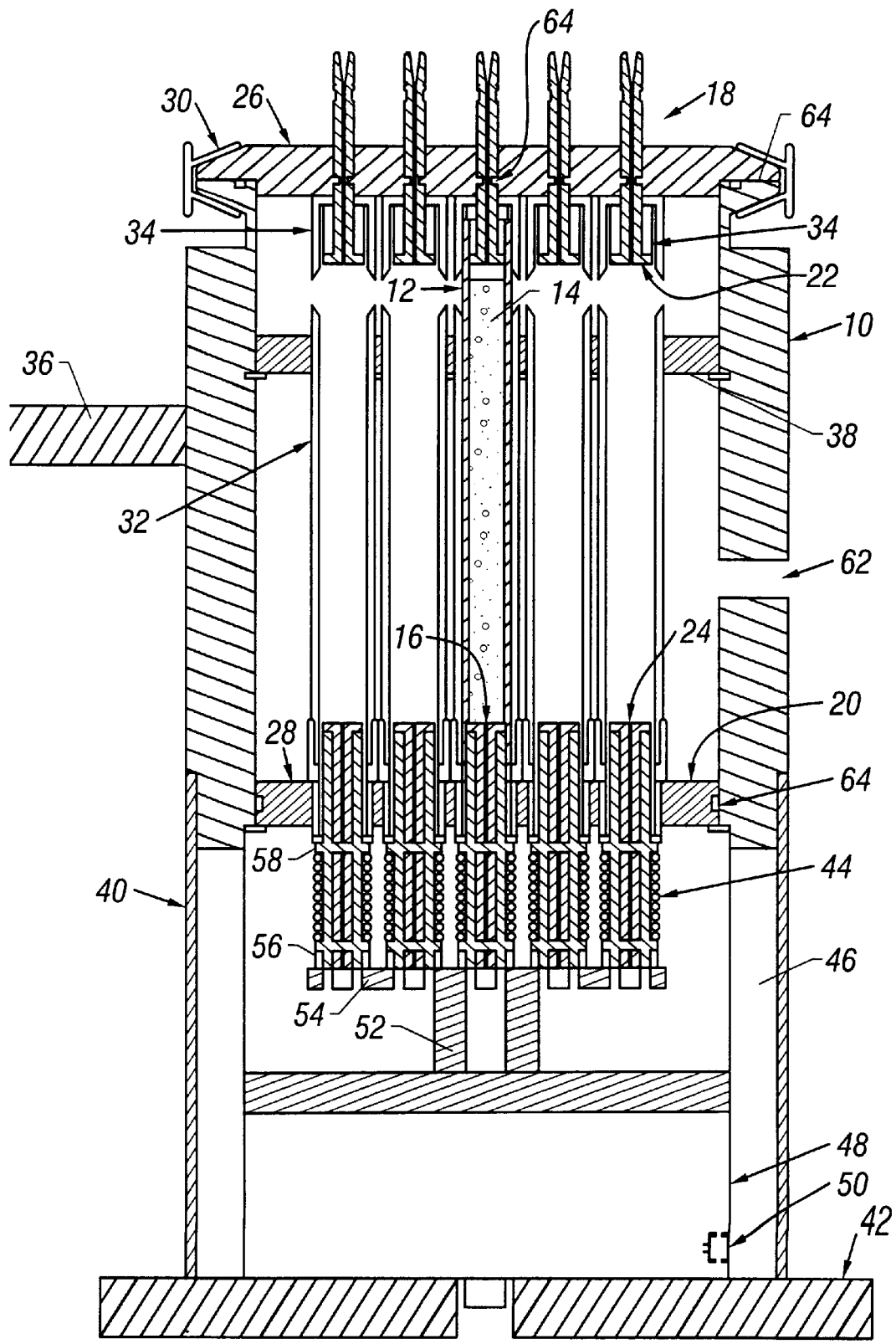
FIG. 1B is a diagrammatic vertical-sectional view, taken at IB—IB of FIG. 1A, of an apparatus for sealing a plurality of chromatography columns according to the invention.

Referring to FIGS. 1A–1D, there is shown an apparatus employing pressure containment vessel 10 for enclosing and providing pressure to the external walls of a plurality of chromatography columns, such as chromatography column 12. Column 12 is cylindrical and contains media bed 14 that is bounded axially at the top and bottom by porous plates 16. Chromatography columns are sealed by upper sealing assembly 18 and lower sealing assembly 20, which have connections for sample inflow and outflow tubing. Upper sealing assembly 18 has a plurality of upper sealing heads 22, (see FIG. 1C). Lower sealing assembly 20 has a plurality of lower sealing heads 24, (see FIG. 1D). Both upper and lower sealing heads define flowpaths for the passage of liquids. The structure and operation of the sealing heads are described below with reference to FIGS. 4A–4B.

Upper sealing assembly 18 includes upper plate 26 and lower sealing assembly 20 includes lower plate 28. Upper plate 26 contains a plurality of openings through which upper sealing heads 22 are sealably fitted. Upper plate 26 is sealably connected to pressure containment vessel 10 with clamps 30. Lower plate 28 contains a plurality of openings through which lower sealing heads 24 are sealably fitted. Guides 32 and upper guides 34 retain chromatography columns in their proper positions. Guides 32 and upper guides 34 are tubular. Transverse support rod 36 may be connected to pressure containment vessel 10, to provide stability to the apparatus.

Upper guides 34 are attached to upper plate 26. Guides 32 are attached to lower plate 28, and guide support 38 is connected to pressure containment vessel 10. Pressure containment vessel 10 is connected to skirt 40, which is, in turn, mounted on base 42.

Figure 1C:
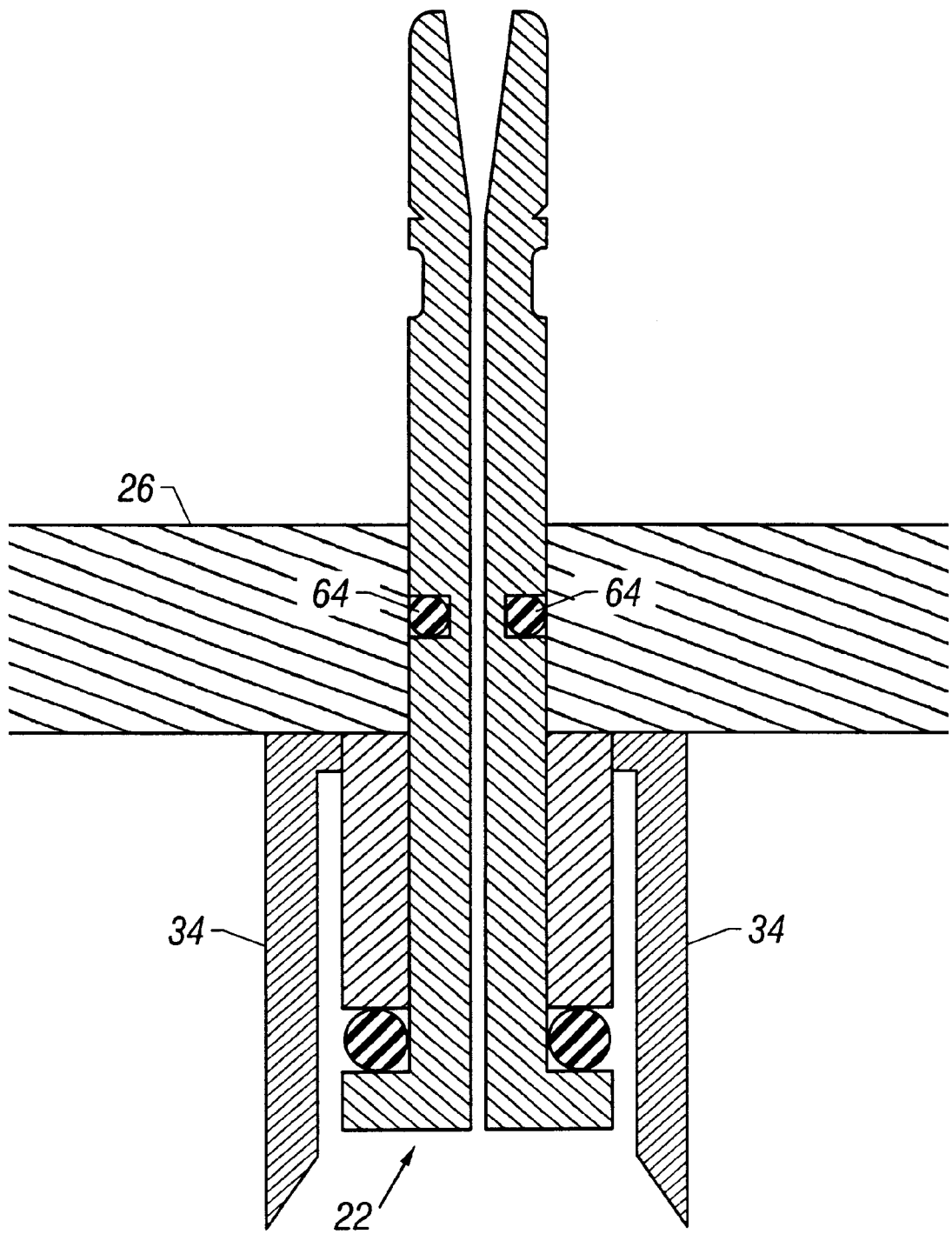
FIG. 1C is a diagrammatic vertical-sectional view of a part of an apparatus for sealing a plurality of chromatography columns according to the invention.

Upper sealing heads 22 and lower sealing heads 24 create seals with chromatography columns such as column 12, when sufficient compressive force is applied to the sealing heads. (The disposition of one of upper sealing heads 22 is shown in FIG. 1C.) Compressive force is applied to lower sealing heads 24, which are slidably and sealably connected to lower plate 28. Lower sealing heads 24 are capable of sliding axially, relative to lower plate 28, independently with respect to each other. Lower sealing heads 24 are thus pressed against porous plates 16 which bound the media 14 contained within chromatography columns such as column 12. Compressive force is thus transmitted through the chromatography columns to upper sealing heads 22. Compressive force acting on both lower sealing heads 24 and upper sealing heads 22 effects a seal at both ends of the chromatography columns between the sealing heads and the inner surfaces of the columns by radial expansion of elastomeric sealing rings as described below with reference to FIGS. 4A–4B.

Figure 1D:
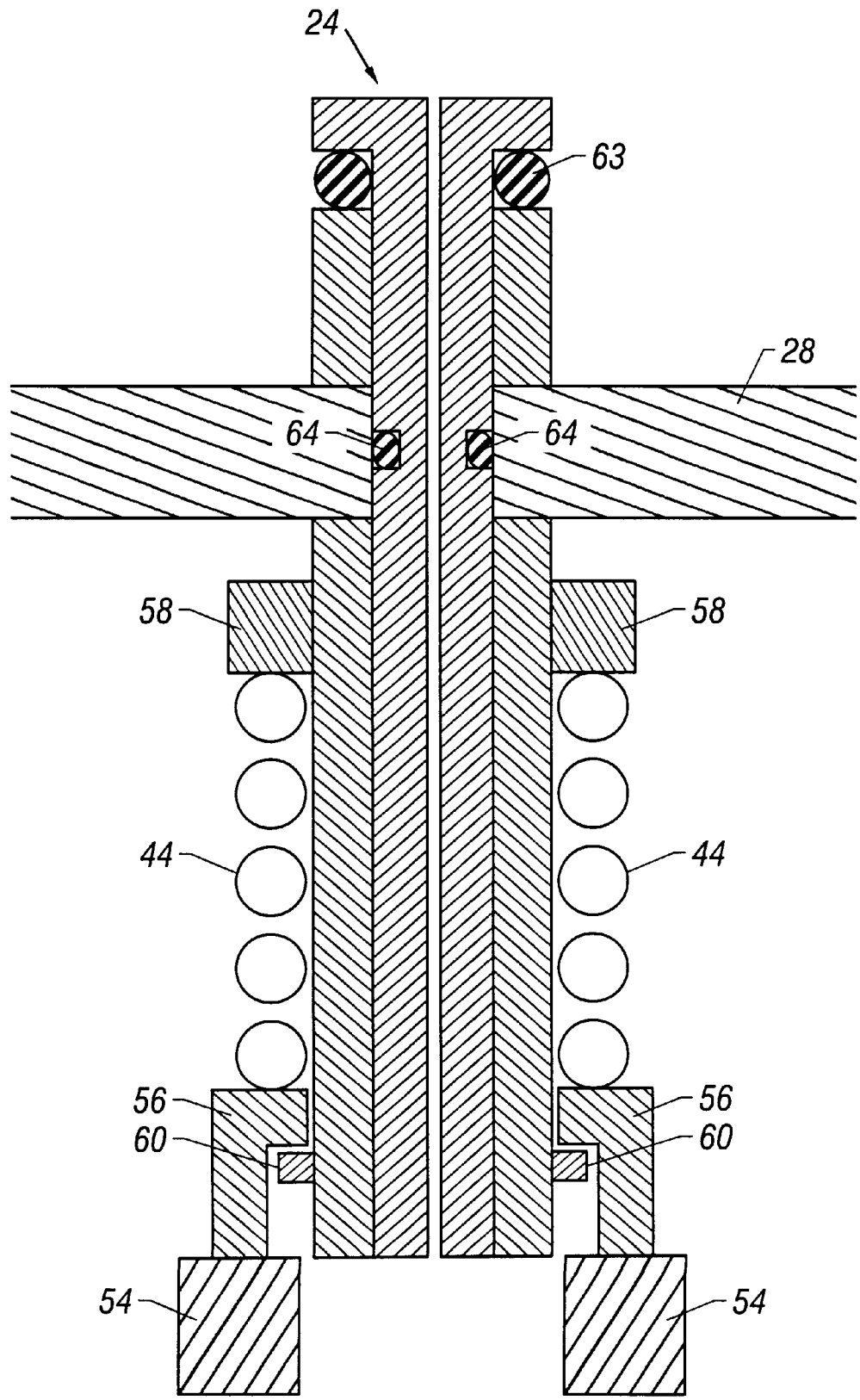
FIG. 1D is a diagrammatic vertical-sectional view of a part of an apparatus for sealing a plurality of chromatography columns according to the invention.

In the embodiment of FIGS. 1A–1D, compressive force is supplied to lower sealing heads 24 through springs 44 by piston 46 in reaction to the introduction of pressurized fluid into piston chamber 48 through piston activation inlet 50. Introducing pressurized fluid into piston chamber 48 causes piston 46 to rise. Piston 46 is slidably adjacent to the walls of piston chamber 48. Transmission members 52 are connected to piston 46. Transmission members 52 are in contact with transmission plate 54. Transmission plate 54 defines openings through which lower sealing heads 24 may pass, as transmission plate 54 rises in response to the motion of piston 46. Transmission plate 54 is in contact with spring compression members 56, which are slidably adjacent to and surround lower sealing heads 24. (FIG. 1D). Spring compression members 56 are also in contact with springs 44. Compressive force exerted on springs 44 by spring compression members 56 is transmitted to lower sealing heads 24 because the motion of springs 44 is impeded by upper retaining rings 58, which are fixedly connected to lower sealing heads 24.

Preferably, springs 46 are retained in a compressed state, when bounded by upper retaining rings 58 and by spring compression members 56. Spring compression members 56 are, in turn, bounded by lower retaining ring 60 as seen in FIG. 1D, thus providing a minimum preload force between spring compression members 56 and sealing heads 24. Lower retaining rings 60 are fixedly connected to lower sealing heads 24.

Sealing elements 64 provide pressure seals between parts of the apparatus that contact each other, such as: between upper plate 26 and the pressure containment vessel 10; between lower plate 28 and pressure containment vessel 10; and between any of upper sealing heads 22 and upper plate 26; between any of lower sealing heads 24 and lower plate 28. Appropriate parts (e.g., upper plate 26, lower plate 28, pressure containment vessel 10, upper sealing heads 22, or lower sealing heads 24) may define troughs for retaining sealing elements 64.

In operation of the embodiment of FIGS. 1A–31D, chromatography columns, such as column 12, are inserted into guides 32 and mated with lower sealing heads 24. Upper sealing assembly 18 is then placed on pressure containment vessel 10 so that each of upper guides 34 surrounds one of the columns and upper sealing heads 22 mate with the columns. Clamp 30 is attached to connect upper plate 26 to pressure containment vessel 10. Introducing a fluid into piston chamber 48 through inlet 50 increases the pressure in chamber 48 and creates an upward force on piston 46 which is transmitted through transmission members 52 to transmission plate 54 and spring compression members 56 to springs 44. Springs 44, in turn, transmit the compressive force to upper retaining rings 58 and lower sealing heads 24 through the porous plates and media of the columns, to upper sealing heads 22 and against upper plate 26. The compression of lower sealing heads 24 and the compression of upper sealing heads 22 causes them to form seals with the columns by the radial expansion of rings 63. The compressive force supplied by piston 52 also provides axial compression to the media in the columns. In order to provide radial compression to flexible chromatography columns, pressurized fluid is introduced through pressure containment vessel 10 through radial compression inlet 62. Radial compression helps to provide uniform packing for chromatography media contained within flexible columns.

In the embodiment of FIGS. 1A–1D, activating piston chamber 48 moves piston 46, transmission members 52, and spring compression members 56 upward to apply compressive force to lower sealing heads 24 and upper sealing heads 22.

Figure 2:
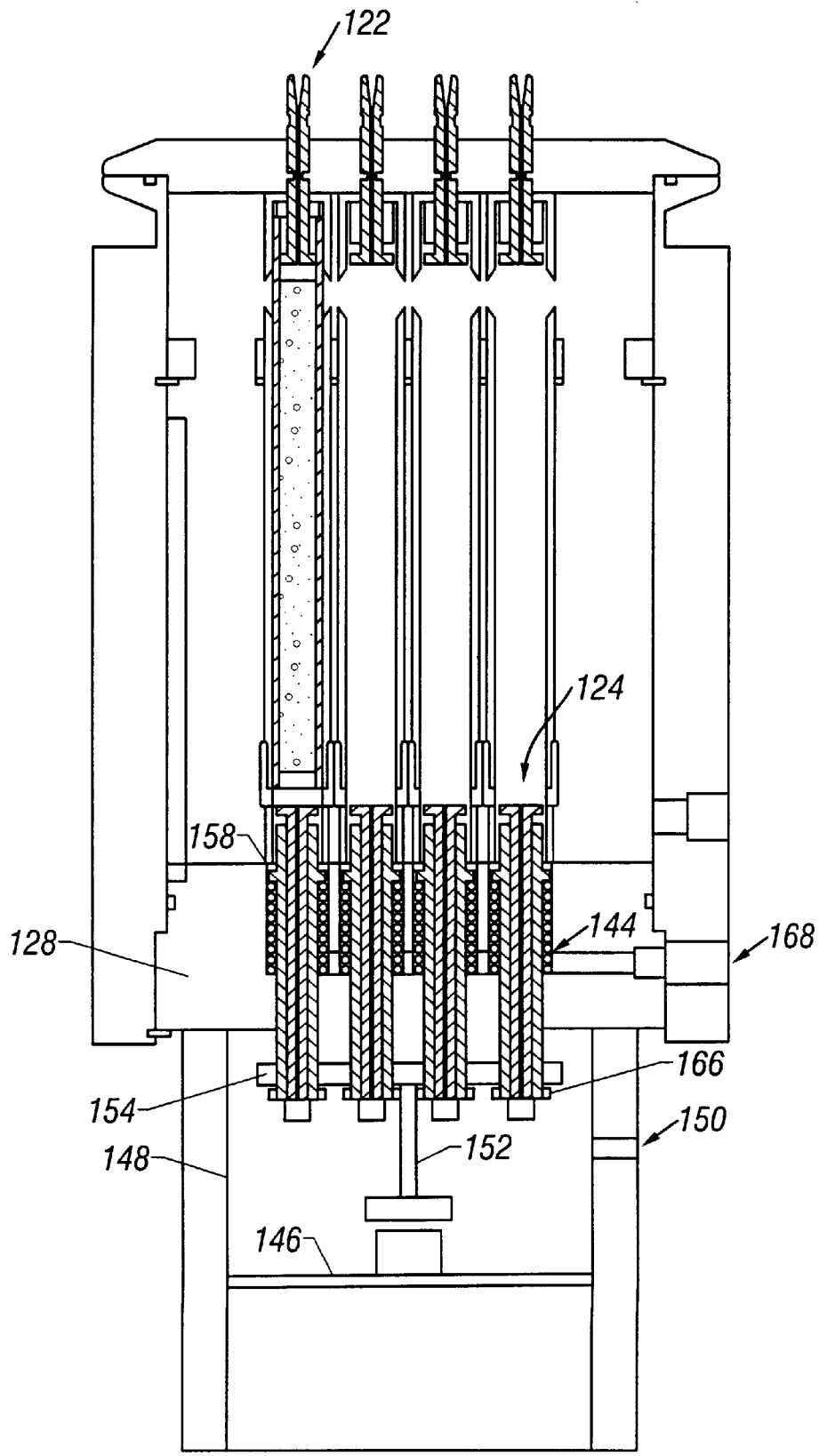
FIG. 2 is a diagrammatic vertical-sectional view of an alternate embodiment of an apparatus for sealing a plurality of chromatography columns according to the invention.

Referring to FIG. 2, in alternate preferred embodiments, springs 144 are disposed so that they provide the compressive force required to activate both upper sealing heads 122 and lower sealing heads 124, unless springs 144 are deactivated by piston 146. In the embodiment shown in FIG. 2, this is achieved by situating springs 144 within recesses defined by lower plate 128. Compressive forces are communicated to lower sealing heads 124 when springs 144 are compressed between lower plate 128 and upper retainers 158. Upper retainers 158 are in fixed relation to lower sealing heads 124. Piston 146 is disposed within piston chamber 148 so that the introduction of a pressurized fluid through piston activation inlet 150 draws transmission member 152, transmission plate 154, and lower sealing heads 124 away from upper sealing heads 122, thus reducing axial compression in upper sealing heads 122, lower sealing heads 124, and media 114 in columns such as column 112. Transmission plate 154 may be fixed to lower sealing heads 124. Preferably, transmission plate 154 is slidably adjacent to lower sealing heads 124, yet retained by retaining members 166, so that forces affecting transmission plate 154 are transmitted to lower sealing heads 124 and springs 144. In this embodiment, loss or variation of fluid pressure in piston chamber 148 does not affect the quality of the seals between upper sealing heads 122 or lower sealing heads 124 and the columns. In the embodiment of FIG. 2, lower plate 128 defines drain passage 168 to permit the egress of any liquids that accumulate within recesses defined by lower plate 128.

In the alternate preferred embodiment of FIGS. 3A–3E, containment structures 232 define tubular openings 272 that are sized to slidably receive chromatography columns 212 containing media 214 bounded by upper porous plates 216 and lower porous plates 217. Containment structures 232 are slidably mounted to vertical rails 238, so that containment structures 232 may slide vertically relative to the frame elements. Lateral frame elements 210 are fixed to vertical rails 238 opposed to containment structures 232.

Lower sealing assembly 220 includes lower plate 228, a plurality of sealing heads 224 slidably mounted through lower plate 228, and springs 244 contained within lower plate 228. The disposition of one of lower sealing heads 224 is shown in detail in FIG. 3E. Lower sealing heads 224 have upper retaining projections 258 (FIG. 3E) set against springs 244. The retaining projections 258 can slide relative to lower plate 228. Lower sealing heads have a structure similar to that shown schematically in FIGS. 4A–4B.

Upper sealing assembly 218 includes upper plate 234, upper frame element 226, and upper sealing heads 222. Upper frame element 226 is slidably mounted on horizontal rails 274 so that upper sealing assembly 218 can slide into or out of alignment with lower sealing assembly 220. Horizontal rails 274 are fixed to upper frame elements 278. Upper sealing heads 222 have a structure similar to that shown schematically in FIGS. 5A–5B.

The embodiment of FIGS. 3A–3E also has piston 246 which is slidably adjacent to piston chamber 248. Piston 246 is pivotally connected to arm 276, which is in turn pivotally connected to transmission member 252. Arm 276 can pivot about axis 282. Transmission member 252 is slidably adjacent to guide 280 and is connected to transmission plate 254. Transmission plate 254, in turn, abuts lower plate 228. Lower sealing heads 224 pass through and can slide relative to transmission plate 254.

Figure 3A:
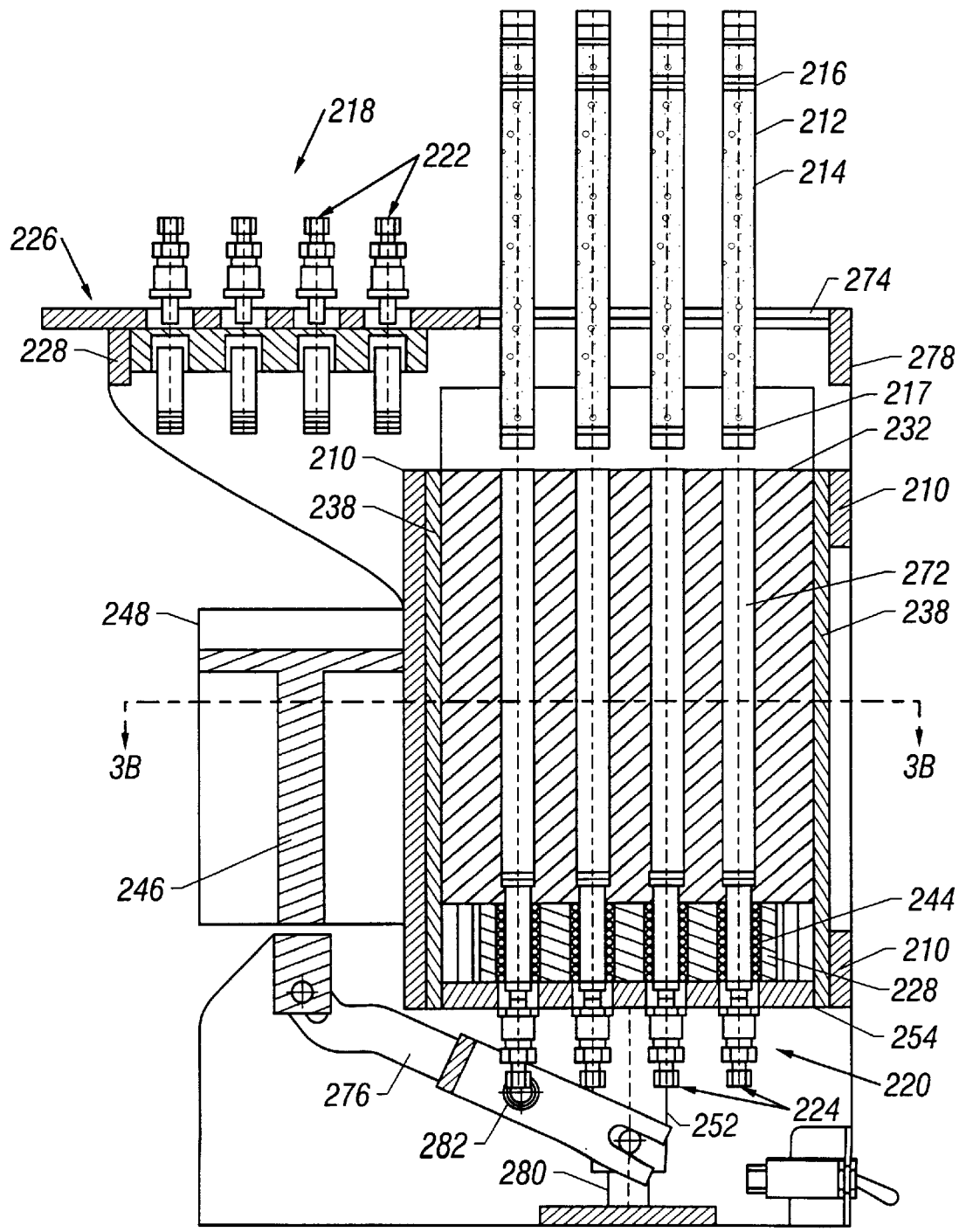
FIG. 3A is a diagrammatic vertical-sectional view of an alternate embodiment of an apparatus for sealing a plurality of chromatography columns according to the invention.
Figure 3B:
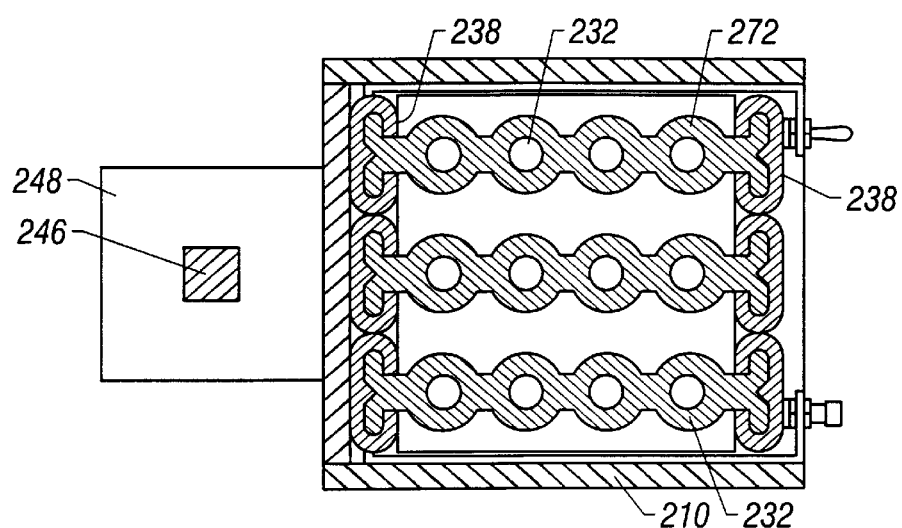
FIG. 3B is a diagrammatic horizontal-sectional view, taken at IIIB—IIIB of FIG. 3A, of the FIG. 3A embodiment.
Figure 3C:
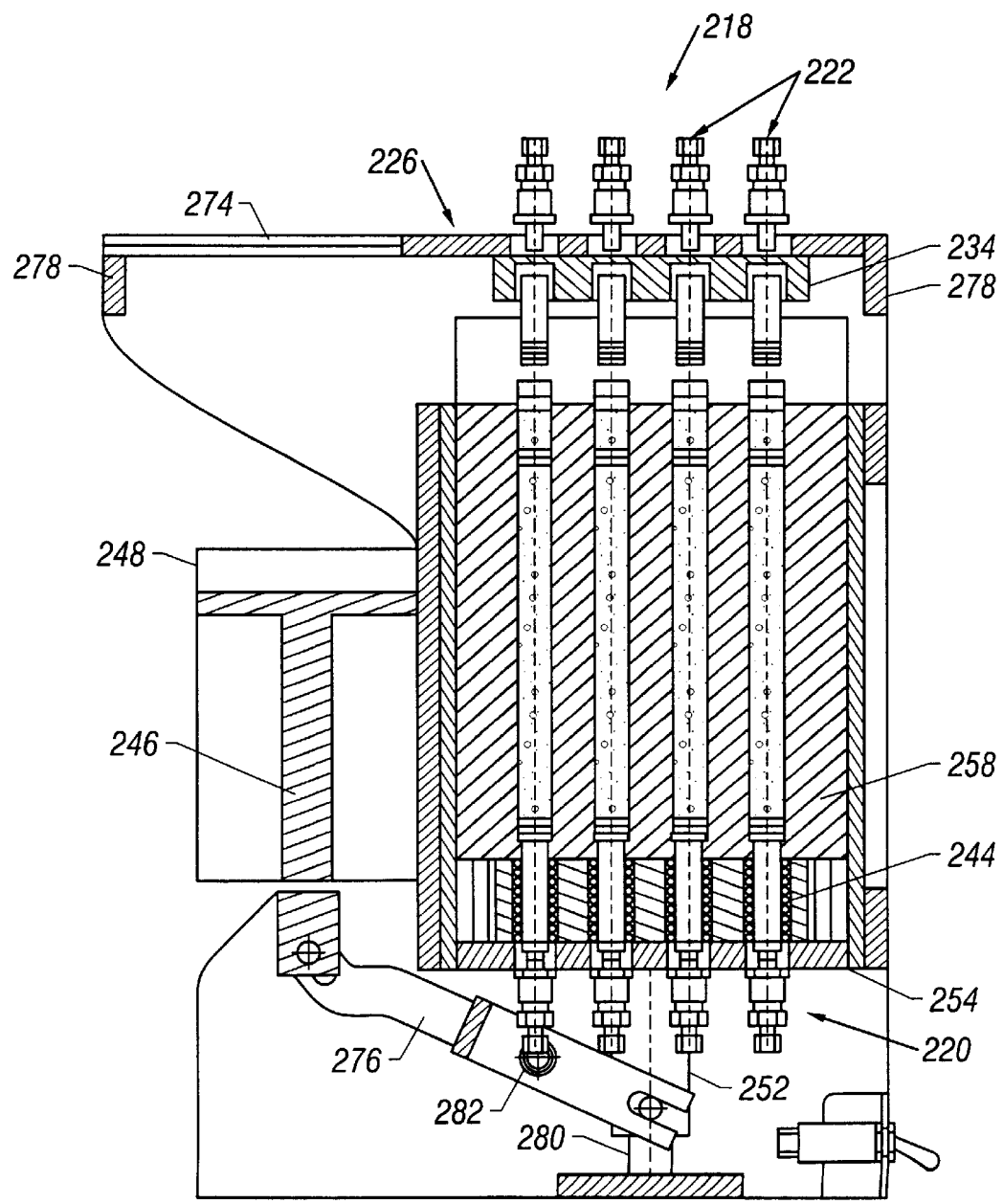
FIG. 3C is a diagrammatic vertical-sectional view of the FIG. 3A embodiment prior to connecting of an upper sealing assembly.

In operation of the embodiment of FIGS. 3A–3E, while upper sealing assembly 218 is out of alignment with lower sealing assembly 220, chromatography columns 212 are placed into tubular openings 272 so that lower sealing heads 224 enter columns 212. FIG. 3A shows columns 212 positioned for entry into tubular openings 272. Upper sealing assembly 218 is slid into alignment with lower sealing assembly 220, as seen in FIG. 3C. With the sealing assemblies 218, 220 aligned, piston 246 is activated so that it descends relative to piston chamber 248 and causes arm 276 to pivot about axis 282. The angular movement of arm 276 raises transmission member 252 relative to guide 280. The upward movement of transmission member 252 lifts transmission plate 254, lower plate 228, and containment structures 232, the last of which slides relative to vertical rails 238.

Figure 3D:
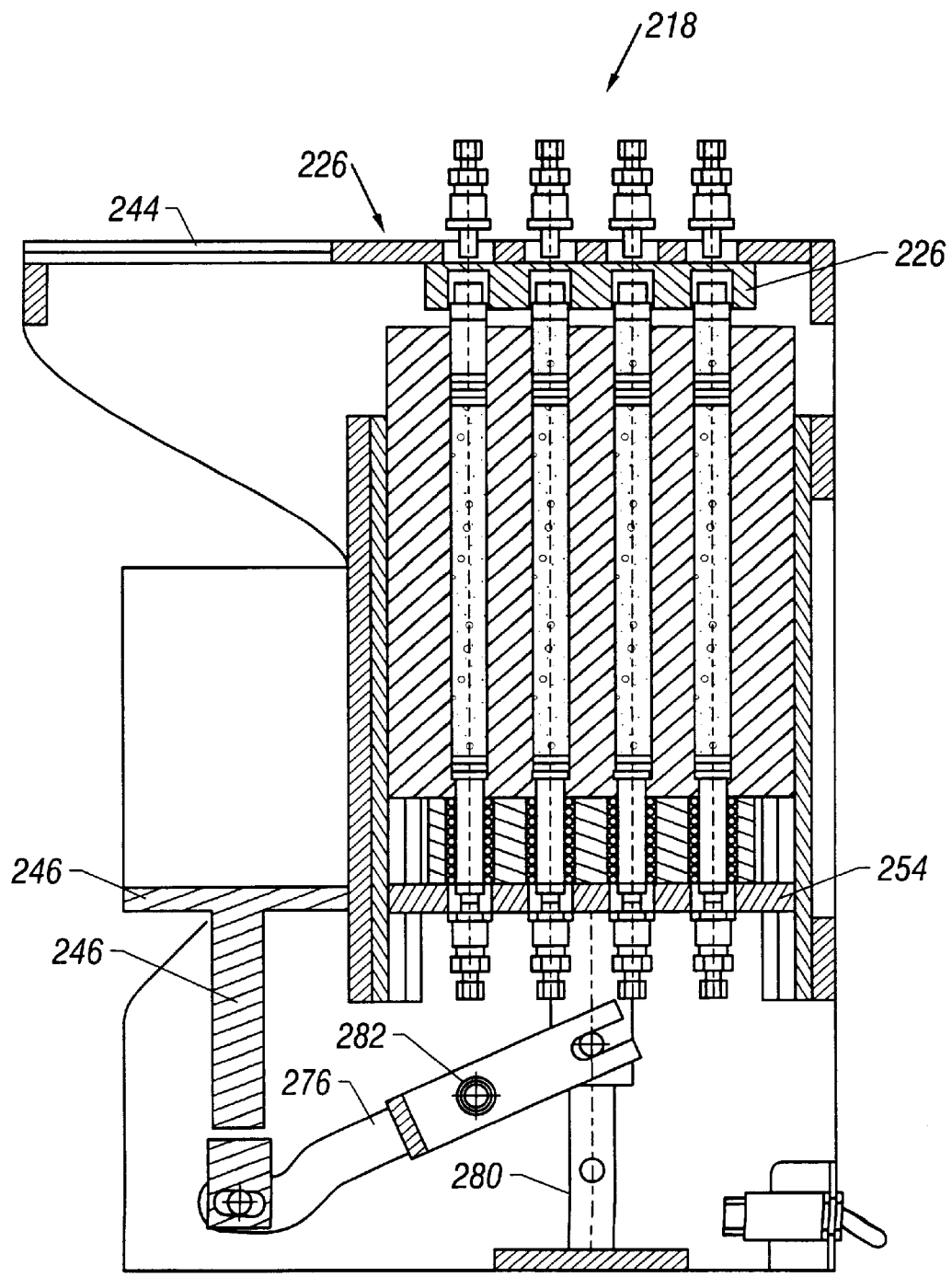
FIG. 3D is a diagrammatic vertical-sectional view of the FIG. 3A embodiment after connection of the upper sealing assembly.
Figure 3E:
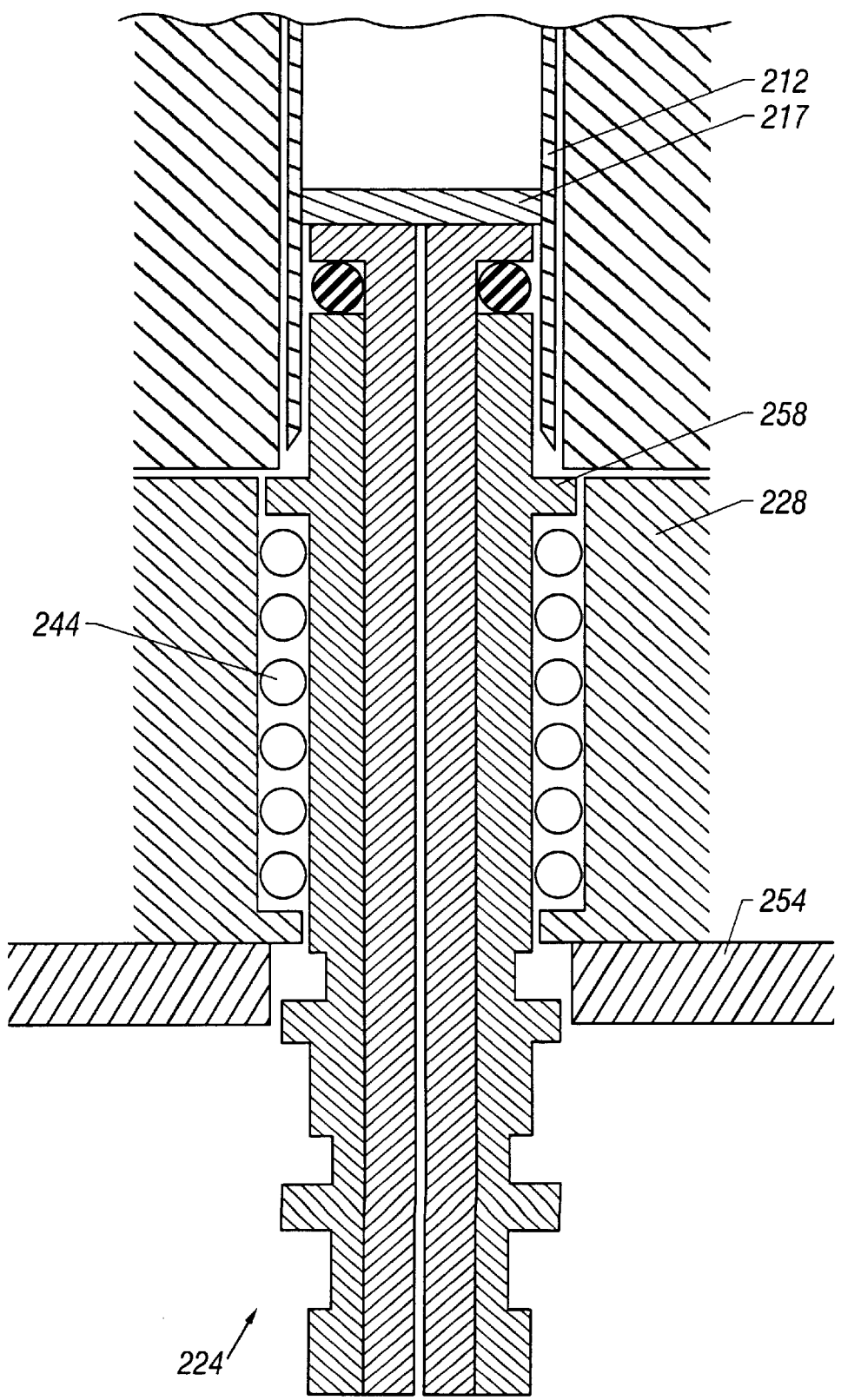
FIG. 3E is a diagrammatic vertical-sectional view of a part of an alternate embodiment of an apparatus for sealing a plurality of chromatography columns according to the invention.

Along with lower plate 228, springs 244 are lifted, thus transmitting force to lower sealing heads 224 through retaining projections 258 (FIG. 3E). Because of the upward force conveyed to lower sealing heads 224, columns 212, which fit over lower sealing heads 224, are also lifted.

As seen in FIG. 3D, when columns 212 approach upper sealing assembly 218, upper sealing heads 222 fit into columns 212. Through continued upward movement of columns 212, upper porous plates 216 press against upper sealing heads 218 and lower porous plates 217 press against sealing heads 224, thereby compressing springs 244, until the upper and lower sealing heads 222, 224 seal columns 212.

Any type of sealing head may be used with the invention. Preferably, sealing heads requiring only a low insertion force are employed. The low-insertion-force sealing heads may each create a single seal or a plurality of seals and the sealing heads may be used in conjunction with a sample module that fits into the column.

Figure 4A:
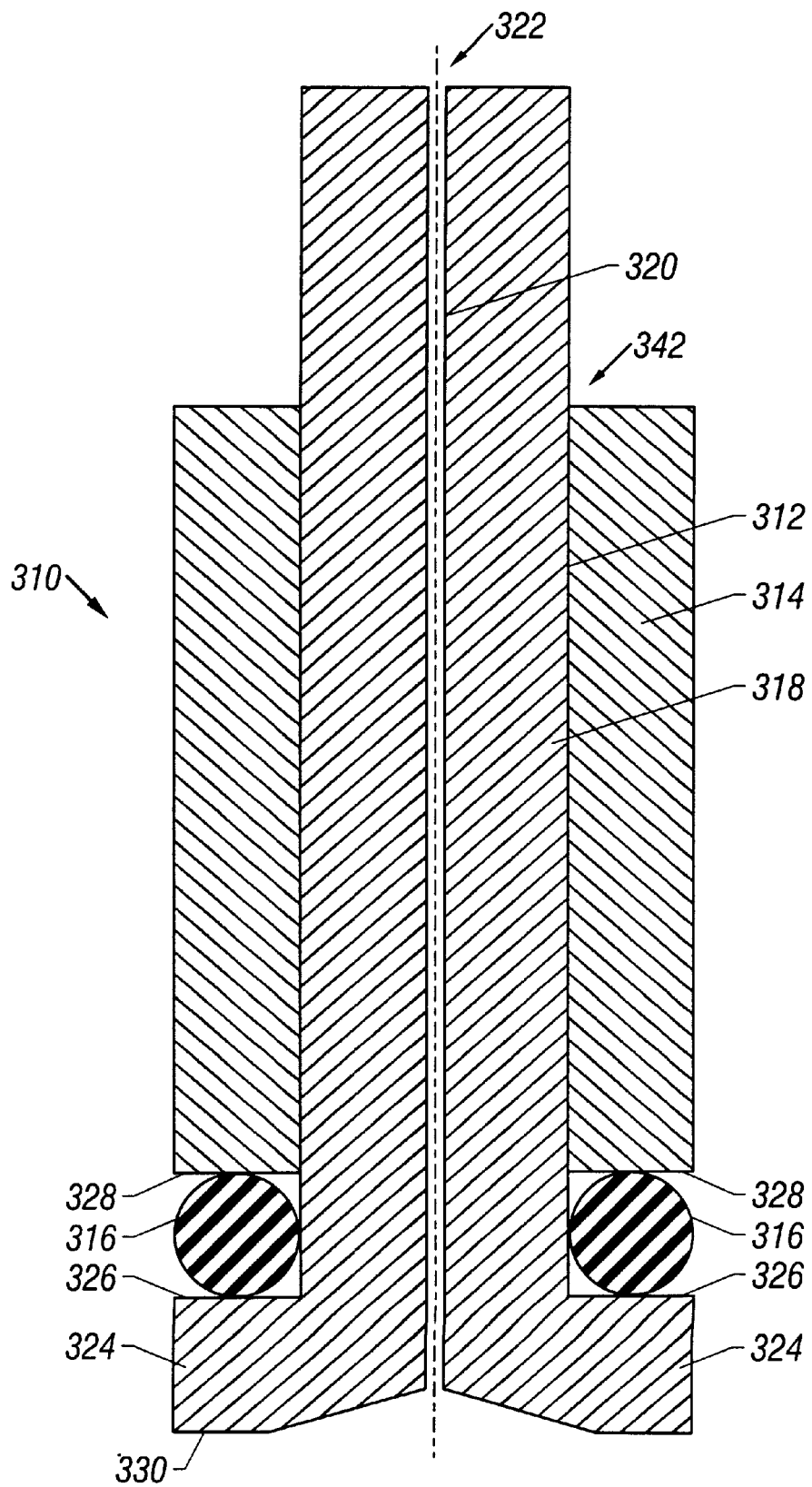
FIG. 4A is a diagrammatic vertical-sectional view of a sealing head that can be used with embodiments of the invention.
Figure 4B:
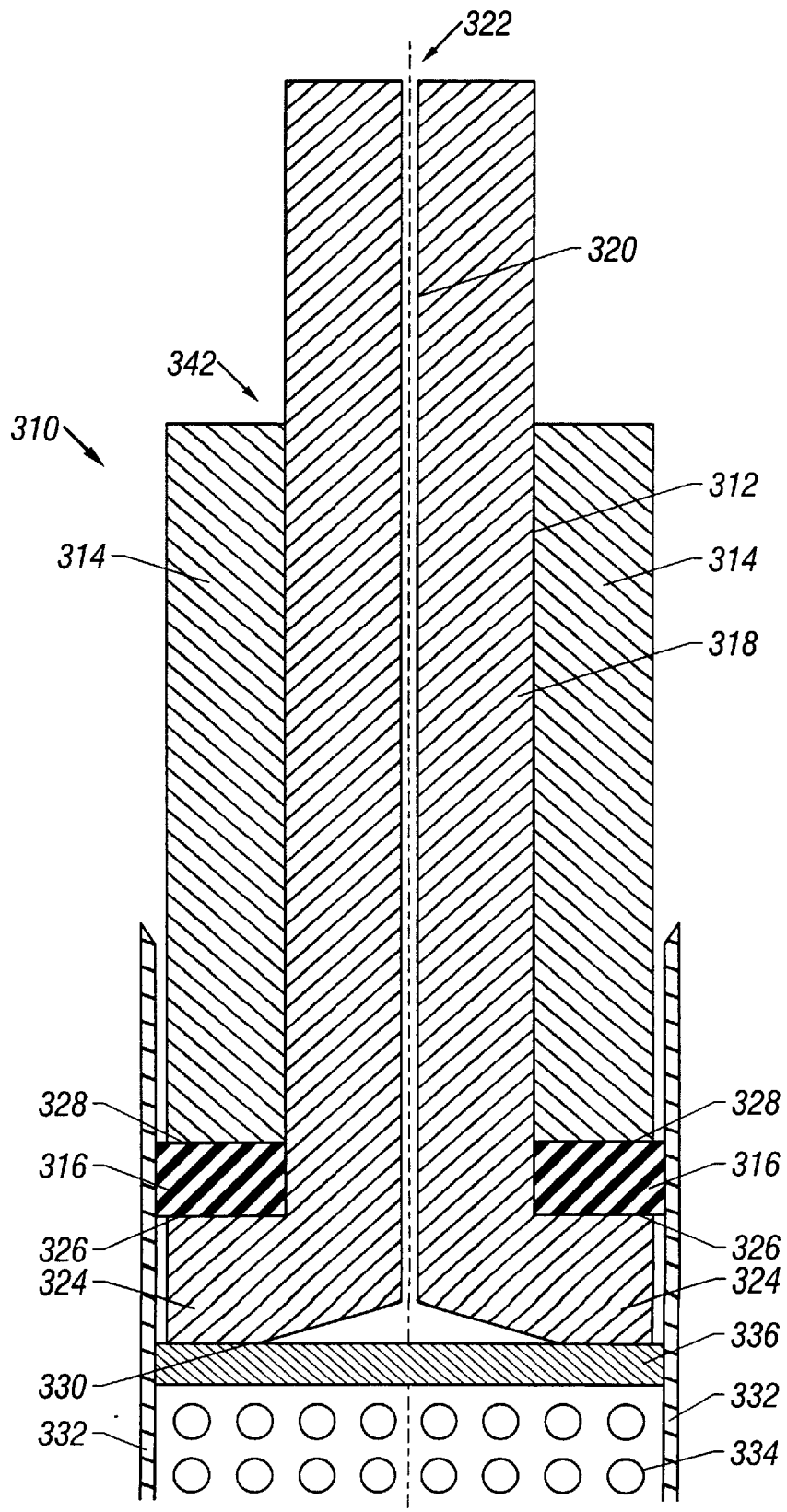
FIG. 4B is a diagrammatic vertical-sectional view of the FIG. 4A sealing head.

Referring to FIGS. 4A–4B, one type of low-insertion-force sealing head 310 contains first head piece 312, second head piece 314 and elastomeric sealing member 316. First head piece 312 has body portion 318 that is slidably fitted into central opening 342 in second head piece 314. Body portion 318 defines flowpath 320, along axis 322, for liquids used in chromatography. First head piece 312 also has cylindrical outwardly extending shoulder 324 that is broader than the central opening in second head piece 314, and contact face 330. Elastomeric sealing member 316 has an annular shape and is disposed between first compression face 326 located on shoulder 324 of the first head piece and second compression face 328 on second head piece 314.

FIG. 4B shows the connection of sealing head 310. To form a sealable connection, sealing head 310 is inserted into an end of chromatography column 332 having media 334 that is bounded axially by porous plate 336. When elastomeric sealing member 316 is not compressed, sealing head 310 slides easily into column 332. After insertion, moving first head piece 312 upward relative to second head piece 314 compresses elastomeric sealing member 316 between first compression face 326 and second compression face 328, thus causing sealing member 316 to expand radially. The radial expansion of elastomeric sealing member 316 causes it to form a seal with column 332. The relative movement of the head pieces can be achieved by compressing second head piece 314 against porous plate 336 and media 334. Such a compressive force will compress elastomeric sealing member 316 against shoulder 324 and will, in turn, compress contact face 330 against porous plate 336.

When employed as an upper sealing head in any of the embodiments of FIGS. 1A–1D, FIG. 2, or FIGS. 3A–3E, the first head piece of a low-insertion-force sealing head is slidable relative to the upper plate and the second head piece is fixedly connected to the upper plate. When employed as a lower sealing head in any of the embodiments of FIGS. 1A–1D, FIG. 2, or FIGS. 3A–3E, the second head piece is slidably connected to the lower plate.

Other embodiments of the invention are within the scope of the claims. E.g., retaining rings and retaining projections can be used interchangeably as retainers.

What is claimed is:

1. An apparatus for sealing a plurality of chromatography columns, each column containing media and having two ends, comprising:

an upper sealing assembly, having a plurality of upper sealing heads, each of said upper sealing heads being sized to receive an end of one of the chromatography columns, each of said upper sealing heads capable of sealing one of the chromatography columns; and a lower sealing assembly, connectable to and alignable with said upper sealing assembly, said lower sealing assembly having a plurality of lower sealing heads aligned with respective said upper sealing heads, each of said lower sealing heads being sized to receive an end of one of the chromatography columns, each of said lower sealing heads capable of sealing one of the chromatography columns.

2. The apparatus of claim 1 wherein each of said upper and lower sealing heads is capable of sealing one of the chromatography columns, upon compression of said upper and lower sealing heads.

3. The apparatus of claim 2, further comprising springs, connected to said lower sealing heads, for applying compressive force to said upper and lower sealing heads that have received the columns.

4. The apparatus of claim 3, further comprising a plurality of upper retainers, each of said upper retainers being fixed to one of said lower sealing heads, each of said springs being connected to one of said upper retainers.

5. The apparatus of claim 4, further comprising a transmission plate, said transmission plate connected to said springs, said transmission plate capable of transmitting forces to said springs.

6. The apparatus of claim 3, further comprising a plurality of spring compression members, each of said spring compression members connected to at least one of said springs, each of said springs capable of being compressed by at least one of said plurality of spring compression members, each of said spring compression members being slidably connected to at least one of said lower sealing heads, said spring compression members being in communication with said transmission plate.

7. The apparatus of claim 6 wherein said springs are maintained in a partially compressed state between said upper retainers and said spring compression members.

8. The apparatus of claim 7 wherein said spring compression members are retained by lower retainers, said lower retainers being in fixed relation to said lower sealing heads.

9. The apparatus of claim 3, further comprising a piston, for applying forces to said springs, and further comprising a pressurizable chamber, said piston being connected to said springs, said piston being slidably connected to and capable of moving in response to pressure changes within said pressurizable chamber.

10. The apparatus of claim 9 wherein said piston is in communication with said transmission plate.

11. The apparatus of claim 9 wherein said piston is in communication with retainers, each of said retainers being in contact with one of said lower sealing members, so that said piston can be moved so as to reduce compression on said upper and said lower sealing heads and to increase compression in said springs.

12. The apparatus of claim 9, further comprising a pivot arm connected to said piston and to said springs, said pivot arm capable of transmitting forces from said piston to said springs.

13. The apparatus of claim 3 wherein said upper sealing assembly includes an upper plate, said upper plate having openings through which said upper sealing heads are fitted, and said lower sealing assembly includes a lower plate, said lower plate having openings through which said lower sealing heads are fitted.

14. The apparatus of claim 13 wherein said springs can be compressed by the movement of said lower plate relative to said lower sealing heads.

15. The apparatus of claim 13 wherein said springs are connected to a side of said lower plate that faces said upper plate, and said springs are between said lower plate and said upper retainers.

16. The apparatus of claim 13 wherein said lower plate defines spaces for retaining said springs, and said springs can be compressed by the movement of said lower sealing heads relative to said lower plate.

17. The apparatus of claim 13, further comprising a pressure containment vessel for enclosing the chromatography columns, said pressure containment vessel having upper and lower openings that are capable of being closed by said upper and lower plates.

18. The apparatus of claim 17 wherein said pressure containment vessel can be pressurized, so as to radially compress the chromatography columns.

19. The apparatus of claim 18, further comprising a radial compression inlet for the introduction of a pressurized fluid to radially compress the chromatography columns.

20. The apparatus of claim 17, further comprising guides for locating columns between opposing pairs of said upper and lower sealing heads.

21. The apparatus of claim 20 wherein said guides are tubular.

22. The apparatus of claim 17, further comprising elastomeric sealing elements disposed so as to create seals between said upper sealing assembly and said pressure containment vessel.

23. The apparatus of claim 22, further comprising sealing elements disposed so as to create seals between said lower sealing assembly and said pressure containment vessel.

24. The apparatus of claim 23, further comprising sealing elements disposed so as to create seals between said upper sealing heads and said upper plate, and between said lower sealing heads and said lower plate.

25. The apparatus of claim 1 wherein said upper sealing heads and said lower sealing heads can be inserted into the ends of the columns with a low insertion force.

26. The apparatus of claim 25 wherein each of said plurality of upper sealing heads and each of said plurality of lower sealing heads has:
a first head piece which is elongated along a longitudinal axis and is sized to fit slidably into a respective one of the chromatography columns, said first head piece having a body, an outwardly extending shoulder, and a contact face, said body defining an elongate flow channel along said axis
a second head piece which is sized to fit slidably into the respective chromatography column, said second head piece defining a first central opening within which said body of said first head piece is fit slidably; and
a first annular elastomeric sealing member at least part of which is situated between said shoulder and said second head piece, said first annular elastomeric sealing member being sized to fit slidably into the respective chromatography column when said first annular elastomeric sealing member is not compressed, said first annular elastomeric sealing member capable of being compressed by the relative movement of said first and second head pieces, so that said first annular elastomeric sealing member expands laterally and forms a seal with the respective chromatography column.

27. The apparatus of claim 26 wherein said first annular elastomeric sealing member is capable of being compressed axially, between said shoulder and said second head piece, by the relative movement of said first head piece and said second head piece so that said first annular elastomeric sealing member expands laterally and forms a seal with the respective chromatography column.

28. The apparatus of claim 26, further comprising:
a third head piece which is sized to fit slidably within the respective chromatography column, said third head piece defining a second central opening within which said body of said first head piece fits slidably; and
a second annular elastomeric sealing member at least part of which is situated between said shoulder and said second head piece, said second annular elastomeric sealing member being sized to fit slidably into the respective chromatography column when said second annular elastomeric sealing member is not compressed, said first annular elastomeric sealing member capable of being compressed between said shoulder and said third head piece, and said second elastomeric sealing member capable of being compressed between said third head piece and said second head piece, so that the relative movement of said first and second head pieces compresses said first and second annular elastomeric sealing members causing said first and second annular elastomeric sealing members to expand laterally and to form seals with the respective chromatography column.

29. The apparatus of claim 28 wherein said first and second annular elastomeric sealing members are capable of being compressed axially, by the relative movement of said first head piece and said second head piece so that said first and second annular elastomeric sealing members expand laterally and form seals with the respective chromatography column.

30. The apparatus of claim 1, further comprising rails connected slidably to said upper sealing assembly, said upper sealing assembly capable of sliding on said rails relative to said lower sealing assembly, in order to align said upper sealing assembly with said lower sealing assembly.

31. The combination comprising:
a plurality of chromatography columns, each of said columns containing media and having two ends;
an upper sealing assembly, including a plurality of upper sealing heads, each of said upper sealing heads being sized to receive an upper end of one of said chromatography columns, each of said upper sealing heads being capable of creating a seal with one of said chromatography columns; and
a lower sealing assembly, connectable to and alignable with said upper sealing assembly, said lower sealing assembly having a plurality of lower sealing heads aligned with respective said upper sealing heads, each of said lower sealing heads being sized to receive a lower end of one of said chromatography columns, each of said lower sealing heads being capable of creating a seal with one of said chromatography columns.

32. The apparatus of claim 31 wherein said upper sealing heads and said lower sealing heads can be inserted into the ends of the columns with a low insertion force.

33. The combination of claim 31 wherein each of said upper and lower sealing heads is capable of creating a seal with one of said chromatography columns, upon compression of said upper and lower sealing heads.

34. The combination of claim 33, further comprising springs, connected to said lower sealing heads, for applying compressive force to said upper and lower sealing heads that have received said columns.

35. The combination of claim 34, further comprising a plurality of upper retainers, each of said upper retainers being fixed to one of said lower sealing heads, each of said springs being connected to one of said upper retainers.

36. The combination of claim 35 wherein said upper sealing assembly includes an upper plate, said upper plate having openings through which said upper sealing heads are fitted, and said lower sealing assembly includes a lower plate, said lower plate having openings through which said lower sealing heads are fitted.

37. The combination of claim 36 wherein said springs are connected to a side of said lower plate that faces said upper plate, and said springs are between said lower plate and said upper retainers.

* * * * *